United States Patent
Nagata (10) Patent No.: US 7,965,819 B2
(45) Date of Patent: Jun. 21, 2011

(54) DEVICE FOR LIMITING FIELD ON WHICH RADIATION IS IRRADIATED

(75) Inventor: Tatsuhiko Nagata, Tokyo (JP)

(73) Assignee: Right Mfg. Co., Ltd., Tokyo (JP)

( * ) Notice: Subject to any disclaimer, the term of this patent is extended or adjusted under 35 U.S.C. 154(b) by 676 days.

(21) Appl. No.: 10/585,919

(22) PCT Filed: Jan. 13, 2005

(86) PCT No.: PCT/JP2005/000294
§ 371 (c)(1),
(2), (4) Date: Aug. 6, 2008

(87) PCT Pub. No.: WO2005/068019
PCT Pub. Date: Jul. 28, 2005

(65) Prior Publication Data
US 2008/0292058 A1    Nov. 27, 2008

(30) Foreign Application Priority Data

Jan. 13, 2004   (JP) .................................. 2004-005922

(51) Int. Cl.
*G21K 1/04* (2006.01)
(52) U.S. Cl. ....................................................... 378/152
(58) Field of Classification Search .................... 378/152
See application file for complete search history.

(56) References Cited

U.S. PATENT DOCUMENTS

| | | |
|---|---|---|
| 6,188,748 B1 | 2/2001 | Pastyr et al. |
| 2002/0108816 A1 | 8/2002 | Taniguchi |
| 2002/0126799 A1 | 9/2002 | Saladin et al. |

FOREIGN PATENT DOCUMENTS

| | | |
|---|---|---|
| JP | 59-191869 | 12/1984 |
| JP | 62-136338 | 6/1987 |
| JP | 03-143455 | 6/1991 |
| JP | 03-268771 | 11/1991 |
| JP | 06-300896 | 10/1994 |
| JP | 07-10282 | 2/1995 |
| JP | 07-204284 | 8/1995 |
| JP | 09-131411 | 5/1997 |
| JP | 2002-186677 | 7/2002 |

(Continued)

OTHER PUBLICATIONS

Supplemental European Search Report, dated Jun. 15, 2007.

(Continued)

*Primary Examiner* — Hoon Song
*Assistant Examiner* — Mona M Sanei
(74) *Attorney, Agent, or Firm* — Staas & Halsey LLP (57) ABSTRACT

An irradiation field limiting device includes a plurality of aperture leaves arranged in a thickness direction, a flexible linear member secured to a thick portion of the aperture leaf, a driver section which drives the linear member a specific amount, and the like. One end of the linear member is secured to an aperture leaf through a connection section tangentially to the outer arc of the aperture leaf, and the other end is connected with a slider provided in a driver section. The slider is connected with a driving source through a connection portion and moves along an axial direction of a drive shaft inserted into a base accompanying rotation of the drive shaft. A load accompanying the movement of the slider is directly transmitted to the linear member, and the aperture leaf is driven a specific amount due to the load.

21 Claims, 7 Drawing Sheets

FOREIGN PATENT DOCUMENTS

| | | |
|---|---|---|
| JP | 2002-210026 | 7/2002 |
| JP | 2002-242968 | 8/2002 |
| JP | 2002-355242 | 12/2002 |
| JP | 2003-093524 | 4/2003 |
| JP | 2004-089214 | 3/2004 |
| JP | 2004-275243 | 10/2004 |

OTHER PUBLICATIONS

International Search Report, dated Apr. 12, 2005.

DEVICE FOR LIMITING FIELD ON WHICH RADIATION IS IRRADIATED

This application is a National Stage Application of International Application No. PCT/JP2005/000294 filed Jan. 13, 2005, which application published in Japanese on Jul. 28, 2005 as WO 2005/068019 A1 under PCT Article 21 (2). The International Application PCT/JP2005/000294 is based upon and claims the benefit of priority from Japanese Patent application No. 2004-005922, filed on Jan. 13, 2004, the entire contents of which are incorporated herein by reference.

FIELD OF THE INVENTION

The present invention relates to an irradiation field limiting device which forms an irradiation field corresponding to the shape of the lesion of a radiotherapy target subject.

BACKGROUND OF THE INVENTION

When applying radiation to the lesion of a radiotherapy target subject, an irradiation field limiting device has been widely used which forms an irradiation field corresponding to the shape of the lesion by limiting the irradiation range.

Japanese (unexamined) Patent Application, No. H06-300896 (hereinafter called "patent document 1") discloses an irradiation field limiting device which includes an aperture block (hereinafter called "aperture leaf") of which the surface of the aperture operation which limits the irradiation range forms a cylindrical surface and which is provided with a rack in the inner circumferential surface, and a pinion which engages the aperture leaf, in which the aperture leaf is driven by transmitting rotation of a motor to the rack and the pinion through a chain or the like.

Japanese Examined Patent Application, No. H07-10282 (hereinafter called "patent document 2") discloses an irradiation field limiting device which includes a plurality of aperture leaves in which grooves and protrusions are formed on the sliding surface, in which the aperture leaves are slidably arranged in the side surface direction to shield radiation passing through the opening between the sliding surfaces.

The irradiation field limiting device disclosed in the patent document 1 has a problem in which the positional accuracy of the aperture leaf decreases due to wear of the rack and the pinion. Therefore, it is difficult to accurately form the irradiation field.

The widths of the rack and the pinion cannot be reduced to a large extent taking durability and the like into consideration (for example, durability significantly decreases when reducing the width to 2 mm or less). This makes it difficult to form an aperture leaf with a reduced thickness. As a result, a large number of aperture leaves cannot be disposed in a limited installation space.

When the shape of the aperture leaf is linear, the aperture leaf operates linearly. Therefore, the aperture leaf can be driven with high accuracy in comparison with the irradiation field limiting device disclosed in the patent document 1 which uses the rack and the pinion by forming a female thread portion in the aperture leaf and forming a male thread portion on a drive shaft connected to a motor.

In this case, when reducing the thickness of the aperture leaf, the diameters of the female thread portion and the male thread portion must be correspondingly reduced. As a result, the female thread portion and the male thread portion exhibit reduced ridge strength. Therefore, it is difficult to ensure stable operation over a long period of time since the ridges easily wear and exhibit poor lubricity.

The irradiation field limiting device disclosed in the patent document 2 has a problem in which it is difficult to form a thin aperture leaf because the groove is formed in the sliding surface of the aperture leaf.

SUMMARY OF THE INVENTION

An object of the present invention is to provide an irradiation field limiting device which allows arrangement of a plurality of thin aperture leaves and can accurately form an irradiation field by accurately driving the aperture leaves.

A first invention provides an irradiation field limiting device which shields radiation from a radiation source by driving a plurality of aperture leaves, arranged in a thickness direction, a specific amount to limit an irradiation field to a desired range, the irradiation field limiting device comprising: a flexible linear member secured to a thick portion of the aperture leaf; and a driver section which drives the linear member.

A second invention provides the irradiation field limiting device according to the first invention, wherein the driver section includes: a base; a drive shaft connected with a driving source through a connection portion and inserted into the base; and a slider which moves along an axial direction of the drive shaft accompanying rotation of the drive shaft and is connected with the linear member.

A third invention provides the irradiation field limiting device according to the second invention, wherein the connection portion includes a torque limiter section which limits transmission of torque equal to or greater than a specific torque.

A fourth invention provides the irradiation field limiting device according to the third invention, wherein the connection portion includes a clutch mechanism which transmits a driving force to the drive shaft or disconnects the driving force from the drive shaft; and wherein the irradiation field limiting device includes a control section which prevents the driving force from being transmitted to the drive shaft using the clutch mechanism when the torque limiter section has operated for a specific period of time.

A fifth invention provides the irradiation field limiting device according to the second invention, wherein the connection portion includes: a clutch mechanism which transmits a driving force to the drive shaft or disconnects the driving force from the drive shaft; and wherein the irradiation field limiting device includes a position detection section which detects a position of the aperture leaf; and a control section which prevents the driving force from being transmitted to the drive shaft using the clutch mechanism to stop movement of the aperture leaf when the position detection section has detected that the aperture leaf has moved to a target position.

A sixth invention provides the irradiation field limiting device according to the second invention, comprising: a driving force transmission section which transmits a driving force of the driving source to a plurality of the drive shafts; a plurality of clutch mechanisms which transmit the driving force to the drive shafts or disconnect the driving force from the drive shafts; and a control section which can drive each of the aperture leaves by transmitting the driving force of the driving source in units of the drive shafts by controlling each of the clutch mechanisms.

A seventh invention provides the irradiation field limiting device according to the second invention, wherein the slider has a female thread portion; and wherein the drive shaft has a male thread portion which engages the female thread portion and moves the slider in the axial direction of the drive shaft by being rotated.

An eighth invention provides the irradiation field limiting device according to the first invention, wherein the aperture leaf is fan-shaped or approximately rectangular.

A ninth invention provides the irradiation field limiting device according to the first invention, wherein the linear member is a continuous metal wire, a wire rope formed by twisting the metal wires, or a hollow pipe.

A tenth invention provides the irradiation field limiting device according to the second invention, comprising: a support shaft provided in the base and disposed approximately in parallel with the drive shaft at a specific interval from the drive shaft; at least one guide which is supported on the support shaft so that the guide can move in an axial direction of the support shaft and maintains a shape of the linear member; and an elastic member which is disposed between the guides and maintains an approximately identical interval between the guides.

An eleventh invention provides the irradiation field limiting device according to the second invention, comprising: an absolute position sensor which measures an absolute position of the aperture leaf and/or the slider; and a high-resolution relative position sensor which measures an amount of movement from a specific position of the aperture leaf and/or the slider measured using the absolute position sensor.

A twelfth invention provides the irradiation field limiting device according to the first invention, wherein the aperture leaves are arranged in a thickness direction so that the aperture leaves can freely move through rolling elements, and a side surface of the aperture leaf protrudes in the thickness direction to form a holding portion which holds the rolling element.

A thirteenth invention provides the irradiation field limiting device according to the twelfth invention, wherein the holding portion forms a straight line and/or a curve to hold the rolling element.

A fourteenth invention provides the irradiation field limiting device according to the twelfth invention, wherein one of the adjacent rolling elements provided on either side of the aperture leaf is disposed at a position close to the radiation source, and the other is disposed at a position away from the radiation source.

A fifteenth invention provides the irradiation field limiting device according to the twelfth invention, wherein the holding portions are disposed at different positions with respect to the irradiation direction, and are repeatedly disposed at an identical position in units of a specific number of the aperture leaves.

A sixteenth invention provides the irradiation field limiting device according to the twelfth invention, wherein the holding portion is a shielding portion which prevents radiation from passing through a space between the aperture leaves adjacent to each other.

A seventeenth invention provides the irradiation field limiting device according to the first invention, comprising a shielding portion which shields radiation in an opening between the aperture leaves adjacent to each other.

An eighteenth invention provides the irradiation field limiting device according to the first invention, wherein the linear members respectively secured to the aperture leaves adjacent in the thickness direction differ in axial direction.

A nineteenth invention provides the irradiation field limiting device according to the eighteenth invention, wherein the driver section drives the aperture leaf of which the axial direction of the linear member is set to be identical in units of a specific number of the linear members.

A twentieth invention provides the irradiation field limiting device according to the first invention, wherein the linear members respectively secured to the aperture leaves adjacent in the thickness direction differ in axial direction and are identical in axial direction in units of a specific number of the linear members; and wherein the irradiation field limiting device includes a plurality of driver units each of which includes a plurality of the driver sections which respectively drive the linear members of which the axial directions are set to be identical in units of a specific number of the linear members.

A twenty first invention provides the irradiation field limiting device according to the first invention, comprising a linear member holding portion which holds the linear member between the aperture leaf and the driver section so that the linear member can move in the axial direction to prevent the linear member from buckling.

A twenty second invention provides the irradiation field limiting device according to the first invention, wherein the linear member drives the aperture leaf while contacting the thick portion, is preliminarily bent in a direction away from a contact portion between the linear member and the thick portion, and presses a portion in contact with the contact portion so that the linear member is prevented from buckling.

EFFECTS OF THE INVENTION

The following effects are obtained by the present invention.

(1) In the irradiation field limiting device according to the present invention, the flexible linear member is secured to the thick portion of each of the aperture leaves arranged in the thickness direction and which shield radiation from the radiation source, and the driver section drives the linear member a specific amount.

According to this irradiation field limiting device, since it suffices that the aperture leaf have such a thickness that the linear member can be secured to the aperture leaf, the thickness of the aperture leaf can be sufficiently reduced.

(2) In the irradiation field limiting device according to the present invention, the driver section includes the slider which moves along the axial direction of the drive shaft accompanying rotation of the drive shaft inserted into the base, and the flexible linear member is connected with the slider.

According to this irradiation field limiting device, since the aperture leaf to which the linear member is secured can be driven due to the movement of the slider accompanying the rotation of the drive shaft, the irradiation field can be accurately formed.

(3) In the irradiation field limiting device according to the present invention, the connection portion includes the torque limiter section (driving force limiting section) which limits transmission of torque (driving force) equal to or greater than a specific torque.

According to this irradiation field limiting device, the torque limiter (torque limiter section) limits the transmission of torque from the motor (driving source) when the oppositely disposed aperture leaves contact the inner side surfaces during the opening/closing operation so that a load equal to or greater than a specific load is applied to the drive shaft, whereby breakage of the motor and the like can be prevented.

(4) In the irradiation field limiting device according to the present invention, the connection portion includes the clutch mechanism which transmits the driving force to the drive shaft or disconnects the driving force from the drive shaft. The control section prevents the driving force from being transmitted to the drive shaft using the clutch mechanism when the torque limiter section has operated for a specific period of time.

According to this irradiation field limiting device, excess wear of the contact surface can be prevented when using a mechanical torque limiter (torque limiter section), for example. Moreover, excess operation of the motor (driving source) in a high load state can be prevented, whereby breakage of the motor can be prevented.

(5) In the irradiation field limiting device according to the present invention, the connection portion includes the clutch mechanism which transmits the driving force to the drive shaft or disconnects the driving force from the drive shaft, and the position detection section which detects the position of the aperture leaf is provided. When the position detection section has detected that the aperture leaf has moved to the target position, the control section prevents the driving force from being transmitted to the drive shaft using the clutch mechanism to stop movement of the aperture leaf.

According to this irradiation field limiting device, since the aperture leaf can be prevented from moving across (i.e. (overrunning)) the target position, the aperture leaf can be stopped in a short time. Specifically, the aperture leaf can be stably controlled and driven.

(6) The irradiation field limiting device according to the present invention includes the driving force transmission section which transmits the driving force of the driving source to the drive shafts, and the clutch mechanisms which transmit the driving force to the drive shafts or disconnect the driving force from the drive shafts The control section controls driving of the aperture leaves by transmitting the driving force of the driving source in units of the drive shafts by controlling the clutch mechanisms.

According to this irradiation field limiting device, the driving force of one driving source can be transmitted to the drive shafts using a pulley, gear, and the like (driving force transmission section), and the drive shaft provided in each base can be driven, for example. The irradiation field limiting device can control and drive the aperture leaves by controlling the clutch mechanisms in units of the drive shafts using the control section. Moreover, since one driving source drives the drive shafts, the space required for the driving source can be reduced, whereby the size of the driver section can be reduced.

(7) In the irradiation field limiting device according to the present invention, the drive shaft has a male thread portion which engages a female thread portion and moves the slider in the axial direction of the drive shaft by being rotated.

This allows the irradiation field limiting device to accurately drive the aperture leaf.

(8) In the irradiation field limiting device according to the present invention, the fan-shaped or approximately rectangular aperture leaf can be accurately driven along a path by securing the flexible linear member to the aperture leaf.

(9) In the irradiation field limiting device according to the present invention, since the linear member is a continuous metal wire, a wire rope formed by twisting the wires, or a hollow pipe, the linear member exhibits flexibility.

(10) In the irradiation field limiting device according to the present invention, the support shaft is provided in the base approximately in parallel with the drive shaft at a specific interval from the drive shaft, and at least one guide maintains the shape of the linear member and can move in the axial direction of the support shaft. The elastic member is disposed to maintain an approximately identical interval between the guides.

According to this irradiation field limiting device, when a load is applied to the linear member in the axial direction when driving the aperture leaf, the linear member can be prevented from buckling in the base.

(11) In the irradiation field limiting device according to the present invention, the absolute position sensor measures the absolute position of the aperture leaf and/or the slider. The high-resolution relative position sensor measures the amount of movement from a specific position of the aperture leaf and/or the slider utilizing the absolute position sensor.

According to this irradiation field limiting device, the reference position (specific position) of the oppositely disposed aperture leaves is measured using the absolute position sensor in a state in which an opening is not formed between the aperture leaves, and the amount of movement of the aperture leaf from the specific position is measured using the relative position sensor, whereby the position of the aperture leaf can be more accurately measured. Moreover, since the position of the aperture leaf is always monitored using the absolute position sensor, an alarm signal can be output to the control section when the absolute position information obtained using the absolute position sensor differs from the amount of movement of the aperture leaf from the specific position measured using the relative position sensor.

(12) In the irradiation field limiting device according to the present invention, the aperture leaves are arranged in the thickness direction so that the aperture leaves can freely move through rolling elements, and the side surface of the aperture leaf protrudes in the thickness direction to form the holding portion which holds the rolling element.

According to this irradiation field limiting device, even if an opening is formed between the aperture leaves, strong radiation can be prevented from passing through the opening. Moreover, the strength of the aperture leaf can be maintained to be equal to or greater than a specific value.

(13) In the irradiation field limiting device according to the present invention, the holding portion forms a straight line and/or a curve to hold the rolling element.

According to this irradiation field limiting device, even when using a thin aperture leaf, the holding portion can be formed by bending or cutting the aperture leaf.

(14) In the irradiation field limiting device according to the present invention, one of the adjacent rolling elements provided on either side of the aperture leaf is disposed at a position close to the radiation source, and the other is disposed at a position away from the radiation source.

According to this irradiation field limiting device, a situation can be prevented in which the total thickness of the aperture leaves arranged in the thickness direction changes due to the rolling element. Since the opening between the aperture leaves is uniformly maintained by the adjacent rolling elements, a situation can be prevented in which the adjacent aperture leaves provided on either side of the rolling element come in contact to increase the frictional resistance, whereby a large amount of load is applied to the linear member, the driver section, and the like.

(15) In the irradiation field limiting device according to the present invention, the holding portions are disposed at different positions with respect to the irradiation direction, and are repeatedly disposed at an identical position in units of a specific number of the aperture leaves.

According to this irradiation field limiting device, since the shape of the aperture leaf can be made identical in units of a specific number of aperture leaves, the holding portions can be formed by repeatedly arranging a specific number of aperture leaves.

(16) In the irradiation field limiting device according to the present invention, the holding portion holds the rolling element and also serves as the shielding portion which prevents radiation from passing through the space between adjacent aperture leaves.

According to this irradiation field limiting device, the holding portion of the rolling element can prevent radiation from leaking through the space between adjacent aperture leaves.

(17) The irradiation field limiting device according to the present invention includes the shielding portion which shields radiation in the opening between adjacent aperture leaves.

According to this irradiation field limiting device, radiation can be prevented from leaking through the space between adjacent aperture leaves.

(18) In the irradiation field limiting device according to the present invention, the linear members respectively secured to the aperture leaves adjacent in the thickness direction differ in axial direction.

According to this irradiation field limiting device, a space sufficient to accommodate the driver section can be provided. Moreover, a driver section of a necessary size can be provided.

(19) In the irradiation field limiting device according to the present invention, the driver section drives the aperture leaf of which the axial direction of the linear member is set to be identical in units of a specific number of the linear members.

According to this irradiation field limiting device, the driver sections can be disposed at specific intervals in units of the axial directions of the linear members. Moreover, since adjacent aperture leaves need not be driven using one driver section, the size of the driver section can be increased to a certain extent. As a result, cost can be reduced, and the durability of the driver section can be maintained.

(20) In the irradiation field limiting device according to the present invention, the linear members respectively secured to the aperture leaves adjacent in the thickness direction differ in axial direction and are identical in axial direction in units of a specific number of the linear members. Each driver unit includes a plurality of driver sections which respectively drive the linear members of which the axial directions are set to be identical in units of a specific number of the linear members.

This allows the irradiation field limiting device to simply contain the driver sections by disposing the driver sections in units of the axial directions of the linear members and providing the driver units containing the driver sections in units of the axial directions of the linear members.

(21) The irradiation field limiting device according to the present invention includes the linear member holding portion which holds the linear member between the aperture leaf and the driver section so that the linear member can move in the axial direction to prevent the linear member from buckling.

This allows the irradiation field limiting device to stably drive the aperture leaf, whereby reliability can be improved.

(22) In the irradiation field limiting device according to the present invention, the linear member drives the aperture leaf while coming in contact with the thick portion of the aperture leaf. The linear member is preliminarily bent in the direction away from the contact portion between the linear member and the thick portion of the aperture leaf, and presses the contact portion between the linear member and the thick portion after being assembled.

According to this irradiation field limiting device, since the linear member can be prevented from buckling in the contact portion between the linear member and the thick portion of the aperture leaf, the aperture leaf can be stably driven, whereby the reliability can be improved.

EXPLANATION OF SYMBOLS

1: radiation source
3: linear member
5: potentiometer
10 and 10-1: driver section
10A, 10B, and 10C: driver unit
11: base
12: driving source
14: drive shaft
15 and 15-1: slider
16: support shaft
17: potentiometer
19: encoder
20 and 40: aperture leaf
21 to 28: rolling element
31: guide
32: elastic member
R1 to R9: roller
100, 100A, and 100B: irradiation field limiting device
A: irradiation field

DETAILED DESCRIPTION OF THE INVENTION

The present invention achieves the object of providing an irradiation field limiting device which allows arrangement of a plurality of thin aperture leaves and can accurately form an irradiation field by accurately driving the aperture leaves by securing a flexible linear member to a thick portion of the aperture leaf and driving the linear member a specific amount using a driver section. Embodiments of the present invention are described below in detail with reference to the drawings.

First Embodiment

Figure 1:
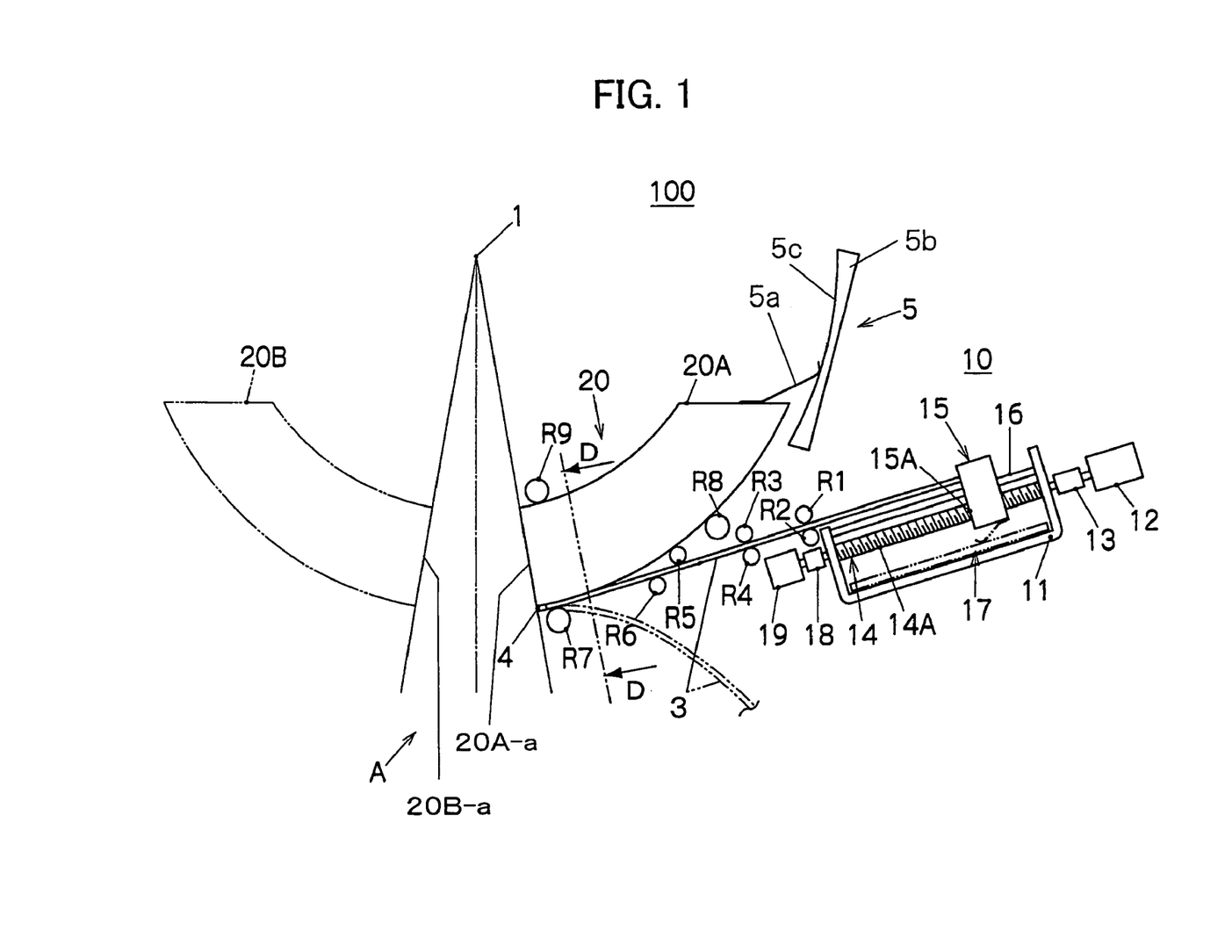
FIG. 1 is a view showing an irradiation field limiting device 100 according to a first embodiment of the present invention.

FIG. 1 is a view showing an irradiation field limiting device 100 according to a first embodiment of the present invention.

The irradiation field limiting device 100 is a device for shielding radiation from a radiation source 1 to limit an irradiation field A to a desired range, the device including an aperture leaf 20, a flexible linear member 3 secured to the thick portion of the aperture leaf 20, a driver section 10 which drives the linear member 3 a specific amount, and the like.

The aperture leaf 20 is formed of an appropriate material (e.g. tungsten) which shields the radiation from the radiation source 1, for example. A plurality of aperture leaves 20 are arranged in the thickness direction. Each aperture leaf 20 includes fan-shaped aperture leaves 20A and 20B oppositely disposed. Members disposed for the aperture leaf 20A are described below for convenience of description. Note that these members are similarly disposed for the aperture leaf 20B.

One end of the linear member 3 is secured to the aperture leaf 20A through a connection section 4 tangentially to the outer arc of the aperture leaf 20A. The other end of the linear member 3 is connected with the driver section 10. When the driver section 10 applies a load to the linear member 3, the linear member 3 is easily warped along the arc of the aperture leaf 20A without buckling.

The linear member 3 may be formed using an appropriate material (e.g., continuous metal wire, wire rope formed by twisting such wires, or hollow pipe) insofar as the material exhibits flexibility.

The linear member 3 drives the aperture leaf 20A while contacting the thick portion of the aperture leaf 20A. The linear member 3 is preliminarily bent in the direction away from the contact portion between the linear member 3 and the thick portion, as indicated by the dash-dot-dot line in FIG. 1, before being secured to the connection section 4, and presses the contact portion between the linear member 3 and the thick portion with a large force after being assembled. This allows the irradiation field limiting device 100 to prevent the linear member 3 from buckling in the contact portion between the linear member 3 and the thick portion of the aperture leaf 20A.

The driver section 10 includes a base 11, a driving source 12, a connection portion 13, a drive shaft 14, a slider 15 connected with the linear member 3, a support axis 16, and the like. The drive shaft 14 is connected with the driving source 12 through the connection portion 13, and inserted into the base 11.

The connection portion 13 includes a clutch mechanism and a torque limiter mechanism (torque limiter section).

The clutch mechanism of the connection portion 13 transmits the driving force of the driving source 12 to the drive shaft 14 through mechanical contact, or disconnects the driving force from the drive shaft 14. When a control section (not shown) moves the aperture leaf 20A to the target position and detects that the aperture leaf 20A has moved to the target position from location information of a potentiometer 5, an encoder 19, and the like (position detection section) described later, the control section prevents the driving force from being transmitted to the drive shaft 14 using the clutch mechanism to stop the movement of the aperture leaf 20A. This allows the irradiation field limiting device 100 to prevent the aperture leaf 20A from moving across (i.e. (overrunning)) the target position. Specifically, the irradiation field limiting device 100 allows the movement of the aperture leaf 20A to be completed within a short time to ensure stable control and drive of the aperture leaf 20A. In the irradiation field limiting device 100, since the drive shaft 14 engages the slider 15, as described later, the position of the slider 15 can be maintained after the clutch mechanism has disconnected the driving force from the drive shaft 14.

The torque limiter mechanism of the connection portion 13 is an overload protection mechanism of which the spring force is adjusted so that the mechanical contact of the clutch mechanism is effected by the spring and the mechanical contact surfaces slide when a load equal to or greater than a specific load has been applied to the drive shaft 14. In the irradiation field limiting device 100, when a load equal to or greater than a specific load has been applied to the drive shaft 14 due to contact between inner side surfaces 20A-a and 20B-a of the aperture leaves 20A and 20B, breakage of the driving source 12 can be prevented by operating the torque limiter mechanism, for example.

The drive shaft 14 has a male thread portion 14A and engages a female thread portion 15A formed in the slider 15.

The slider 15 moves along the axial direction of the drive shaft 14 accompanying rotation of the drive shaft 14. The slider 15 is supported on a support shaft 16 which is disposed approximately in parallel with the drive shaft 14 at a specific interval from the drive shaft 14, whereby rotation around the drive shaft 14 is limited.

Rollers R1 to R6 (linear member holding portions) hold the linear member 3 positioned outside the base 11 and prevent the linear member 3 from buckling. The rollers R1 to R6 specify the path of the linear member 3. Specifically, the irradiation field limiting device 100 according to this embodiment prevents the linear member 3 from buckling by allowing the rollers R1 to R6 to hold the linear member 3 positioned between the aperture leaf 20A and the driver section 10 so that the linear member 3 can move in the axial direction.

Rollers R7 to R9 are disposed along the outer circumferential surface of the aperture leaf 20A to hold the aperture leaf 20A.

Figure 2:
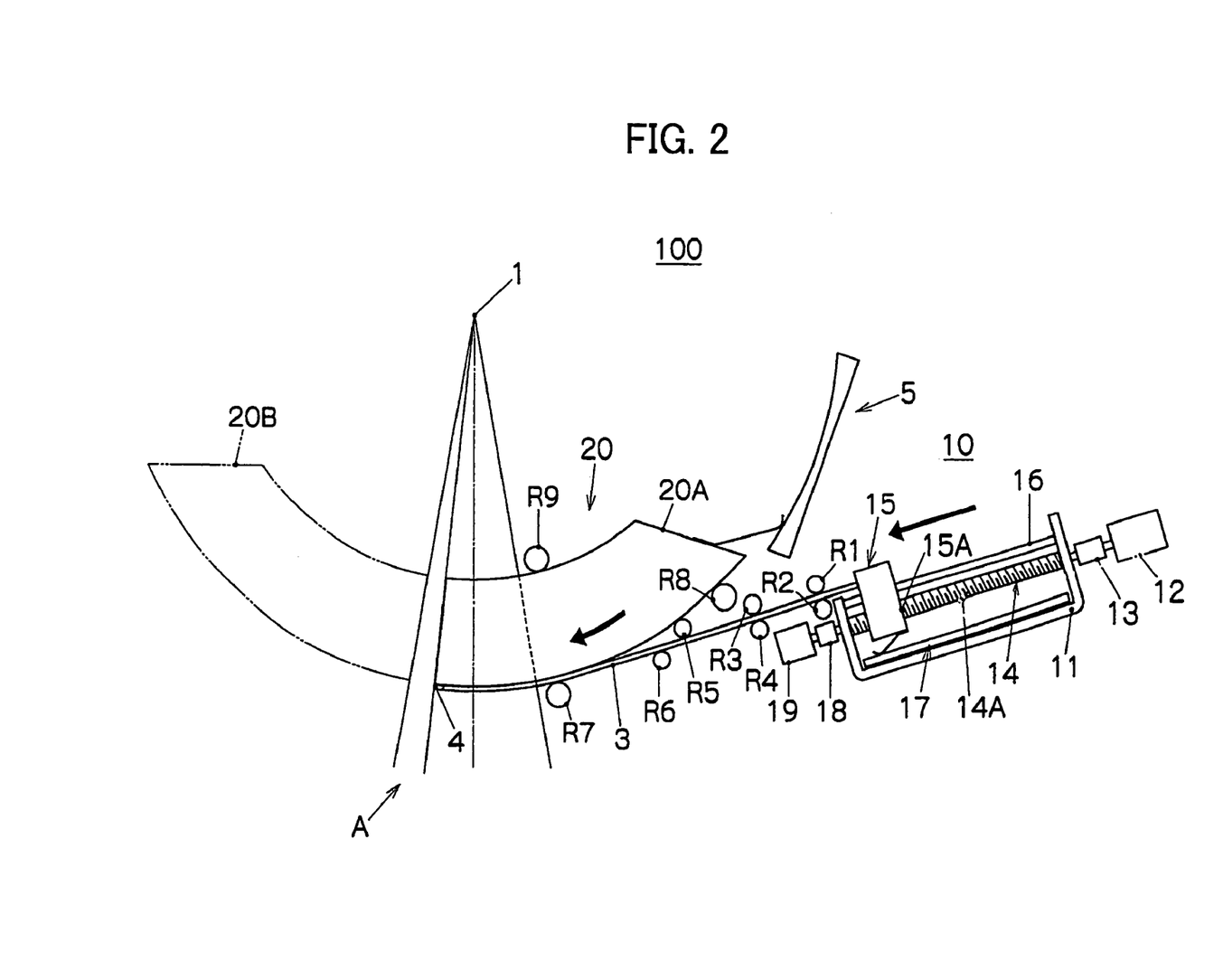
FIG. 2 is a view showing the operation of the irradiation field limiting device 100 according to the first embodiment of the present invention.

Since the linear member 3 is connected with the slider 15 which moves in the axial direction of the drive shaft 14 through engagement between the male thread portion 14A and the female thread portion 15A, the load due to the movement of the slider 15 is directly transmitted to the linear member 3, whereby the aperture leaf 20 is driven a specific amount (see FIG. 2).

In more detail, FIG. 1 illustrates a state in which the linear member 3 is pulled into the base 11 by the slider 15 so that the aperture leaf 20A is pulled in the direction in which the irradiation field A is enlarged.

On the other hand, FIG. 2 illustrates a state in which the linear member 3 is pushed out from the base 11 by the slider 15 so that the aperture leaf 20A is pushed in the direction in which the irradiation field A is reduced (seen the arrow in FIG. 2).

Since the amount of movement of the linear member 3 connected with the slider 15 and the rotation angle of the drive shaft 14 have a proportional relationship, the amount that the aperture leaf 20 is driven can be accurately controlled through accurate control of the rotation angle.

Means for accurately detecting the position of the aperture leaf 20 in order to accurately control the amount that the aperture leaf 20 is driven is described below. The irradiation field limiting device 100 includes a potentiometer 5 (absolute position sensor) and an encoder 19 (relative position sensor) for detecting the position of the aperture leaf 20.

The potentiometer 5 is a linear potentiometer and includes a detection spring 5a and a meter body 5b.

The detection spring 5a is a plate spring formed of phosphorus bronze or the like and secured to the side surface of the aperture leaf 20A. One end of the detection spring 5a contacts the meter body 5b described later.

The meter body 5b is a member formed of a material with a specific electric resistance. The surface 5c of the meter body 5b on the side of the radiation source 1 forms a circumferential surface around the radiation source 1. The surface 5c of the meter body 5b contacts the end of the detection spring 5a which moves to follow the movement of the aperture leaf 20A. This causes the electric resistance of the plate spring 5a and the meter body 5b to change. The potentiometer 5 measures the electric resistance to detect the position of the plate spring 5a. Since the outer circumferential surface of the aperture leaf 20A and the surface 5c of the meter body 5b are circumferential surfaces around the radiation source 1, the position of the aperture leaf 20A can be detected from the diameters of the circumferential surfaces and the position of the plate spring 5a.

The encoder 19 is a detection section which measures the amount of movement from the position of the slider 15, and is provided on the end of the drive shaft 14 opposite to the driving source 12 through a connection portion 18 The encoder 19 measures the amount of movement of the slider 15 by counting the number of pulses generated through the rotation of the drive shaft 14. For example, when the encoder 19 counts 256 pulses during one rotation of the drive shaft 14 and the slider 15 is set to move in an amount of 1 mm by one rotation of the drive shaft 14, the encoder 19 can measure the amount of movement of the slider 15 in units of ⅟256 mm (i.e. 3.9 microns). This allows the irradiation field limiting device 100 to drive the linear member 3 and accurately control and drive the aperture leaf 20A.

An example of the process of detecting and controlling the position of the aperture leaf 20A using the potentiometer 5, the encoder 19, and the like is described below.

The control section (not shown) directs that the inner side surfaces 20A-a and 20B-a of the aperture leaves 20A and 20B come in contact, detects the reference position of the aperture leaf 20A using the potentiometer 5 in a state in which the opening is not formed between the inner side surfaces 20A-a and 20B-a, and stores the reference positions (specific positions) of the aperture leaf 20A and the slider 15. The control section calculates the amount of movement of the aperture leaf 20A and the number of rotations of the drive shaft 14 from the target position of the aperture leaf 20A input from an operation section (not shown), and calculates a specific number of pulses of the encoder 19 corresponding to the number of rotations. The control section drives the driving source 12 to rotate the drive shaft 14, and stops the driving source 12 after the specific number of pulse has been reached. In the above example, when the user has set the target position at a position of 10 mm from the reference position (i.e. the amount of movement is 10 mm), the control section rotates the drive shaft 14 ten times. Therefore, the control section drives the driving source 12 until the encoder 19 counts 2560 pulses (=256 pulses×10). This allows the irradiation field limiting device 100 to accurately detect the current position of the aperture leaf 20A based on the absolute location information of the aperture leaf 20A and the relative position information of the slider 15.

Specifically, the control section can accurately form the irradiation field A by calculating the difference between the position of the aperture leaf 20A detected using the potentiometer 5 and the target position, controlling the rotation of the drive shaft 14 in order to drive the aperture leaf 20A to the target position, and driving the aperture leaf 20A a specific amount. In the above operation, the control section can prevent the aperture leaf 20A from overrunning the target position by disconnecting the driving force from the drive shaft 14 using the clutch mechanism of the connection portion 13 when the control section has recognized that the aperture leaf 20A has reached the target position.

The irradiation field limiting device 100 can monitor the position of the aperture leaf 20A in two ways from the absolute position information of the aperture leaf 20A detected using the potentiometer 5 and the position information measured based on the amount of movement from the position of the aperture leaf 20A detected using the encoder 19. This allows the irradiation field limiting device 100 to output an alarm signal to the control section when the two pieces of position information differ in an amount equal to or greater than a specific amount.

Second Embodiment

Figure 3:
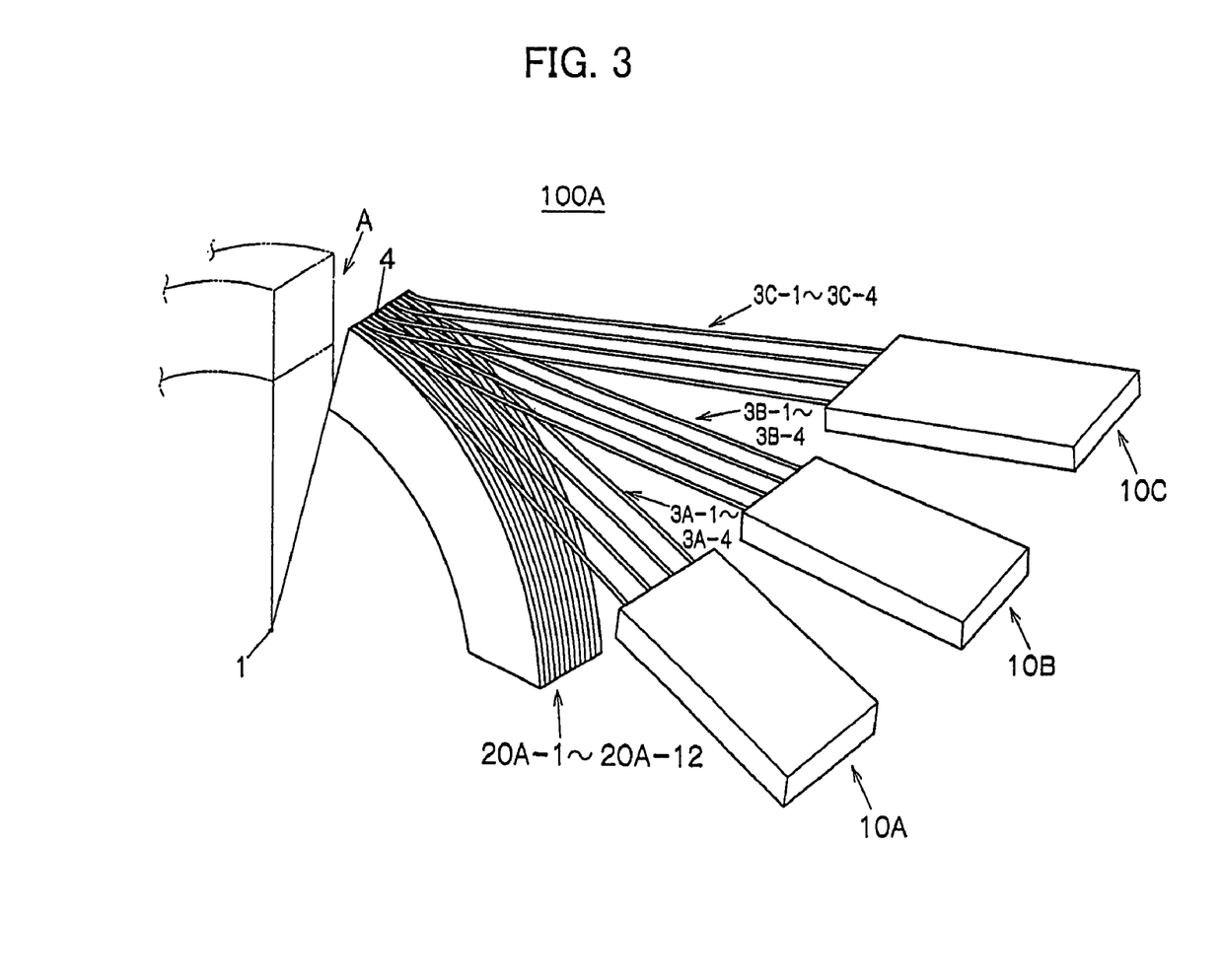
FIG. 3 is a perspective view showing an irradiation field limiting device 100A according to a second embodiment of the present invention.
Figure 4A:
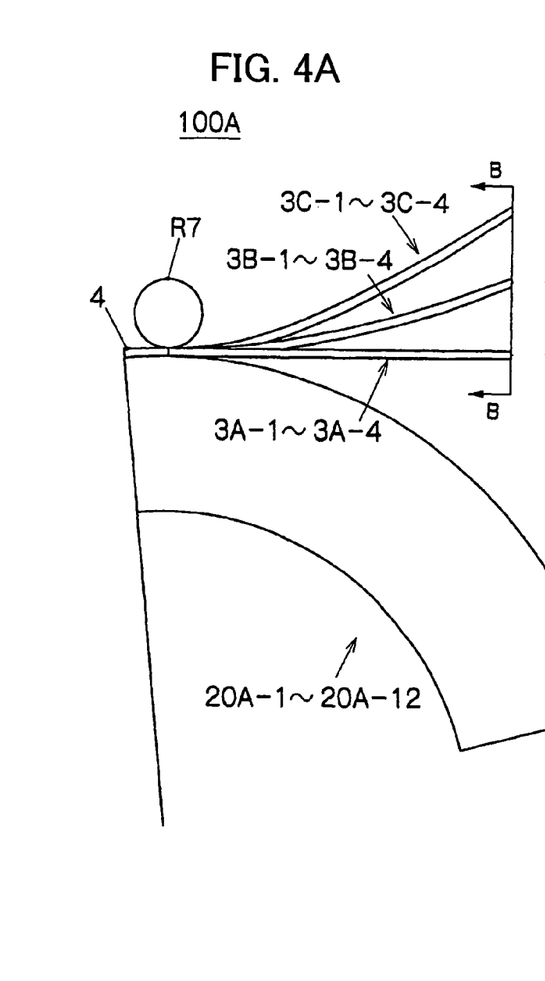
FIG. 4A is a front view and FIG. 4B is a sectional view taken along line B-B of FIG. 4A, showing the irradiation field limiting device 100A according to the second embodiment of the present invention.
Figure 4B:
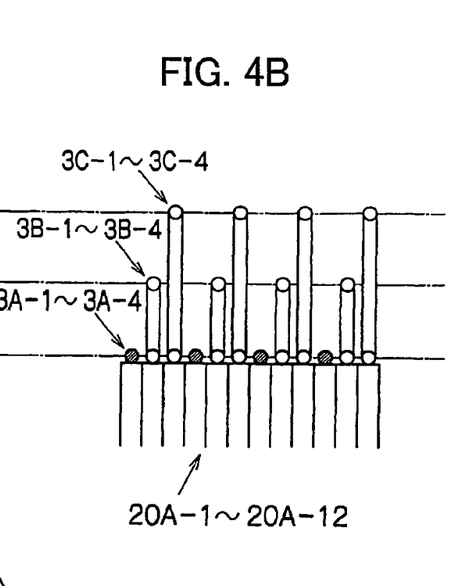

FIG. 3 is a perspective view showing an irradiation field limiting device 100A according to a second embodiment of the present invention. FIG. 4A is a front view and FIG. 4B is a sectional view taken along line B-B of FIG. 4A, showing the irradiation field limiting device 100A according to the second embodiment of the present invention. Note that the same members as those of the above-described irradiation field limiting device 100 are indicated by the same symbols for convenience of description. Description of the functions and the like of these members are appropriately omitted.

The irradiation field limiting device 100A includes a plurality of thin aperture leaves 20A-1 to 20A-12 (about 3 to 5 mm) arranged in the thickness direction, flexible linear members 3 secured to the thick portions of the aperture leaves 20A-1 to 20A-12, a plurality of driver units 10A to 10C which drive the linear members 3 in specific amounts, and the like.

A plurality of sliders 15 (see FIG. 1) are contained in the driver unit 10A, in which the driver sections which respectively drive the linear members 3A-1 to 3A-4 are provided. Likewise, the driver sections which respectively drive the linear members 3B-1 to 3B-4 and 3C-1 to 3C-4 are provided in the driver units 10B and 10C.

As shown in the drawings, the linear members 3A-1 to 3A-4 are almost identical in axial direction. Likewise, the linear members 3B-1 to 3B-4 and the linear members 3C-1 to 3C-4 are almost identical in axial direction, respectively. On the other hand, the linear members 3A-1 to 3A-4, the linear members 3B-1 to 3B-4, and the linear members 3C-1 to 3C-4 differ in axial direction.

As shown the drawings, the linear members 3A-1 to 3A-4 are connected with the driver unit 10A on one end, and are respectively connected with the aperture leaves 20A-1, 20A-4, 20A-7, and 20A-10 on the other end. The linear members 3B-1 to 3B-4 are connected with the driver unit 10B on one end, and are respectively connected with the aperture leaves 20A-2, 20A-5, 20A-8, and 20A-11 on the other end. The linear members 3C-1 to 3C-4 are connected with the driver unit 10C on one end, and are respectively connected with the aperture leaves 20A-3, 20A-6, 20A-9, and 20A-12 on the other end.

As shown the drawings, the linear members 3A-1 and 3B-1 respectively secured to the aperture leaves (e.g., aperture leaves 20A-1 and 20A-2) adjacent in the thickness direction differ in axial direction. Therefore, since the irradiation field limiting device 100A can drive the aperture leaves adjacent in the thickness direction using different driver sections, a plurality of sliders 15 can be provided in the driver sections 10A to 10C of which the size is increased to a certain extent.

In more detail, when the aperture leaf 20A-1 to 20A-12 have a thickness of 5 mm, since one slider 15 must have a thickness of 15 mm, the linear members 3 connected with the sliders 15 are connected with the aperture leaves every three aperture leaves. Specifically, since the irradiation field limiting device 100A allows the driver units 10A to 10C to be disposed at specific intervals, as described above, even if the thicknesses of the aperture leaves 20A-1 to 20A-12 are reduced, the aperture leaves adjacent in the thickness direction can be driven using the driver sections with durability.

Therefore, the irradiation field limiting device 100A allows the driver units 10A to 10C to be disposed at specific intervals in units of the axial directions of the linear members 3A-1 to 3A-4, 3B-1 to 3B-4, and 3C-1 to 3C-4. Moreover, since one driver unit (e.g. driver unit 10A) need not drive the aperture leaves (e.g., aperture leaves 20A-1 and 20A-2) adjacent in the thickness direction, the size of the driver units 10A to 10C can be increased to a certain extent. This reduces cost and maintains the durability of the driver units 10A to 10C.

In the irradiation field limiting device 100A according to this embodiment, the linear members 3 (3A-1 to 3A-4, 3B-1 to 3B-4, and 3C-1 to 3C-4) respectively secured to the aperture leaves 20A (aperture leaves 20A-1, 20A-4, 20A-7, and 20A-10, aperture leaves 20A-2, 20A-5, 20A-8, and 20A-11, and aperture leaves 20A-3, 20A-6, 20A-9, and 20A-12) adjacent in the thickness direction differ in axial direction, and the axial directions are set to be identical in units of a specific number (three in this embodiment) of linear members. The driver units 10A, 10B, and 10C contain the driver sections which respectively drive the linear members of which the axial directions are set to be identical in units of a specific number of linear members. This allows the irradiation field limiting device 100 to simply contain the driver sections by disposing the driver sections in units of the axial directions of the linear members 3 and providing the driver units 10A, 10B, and 10C containing the driver sections in units of the axial directions of the linear members 3.

Third Embodiment

Figure 5:
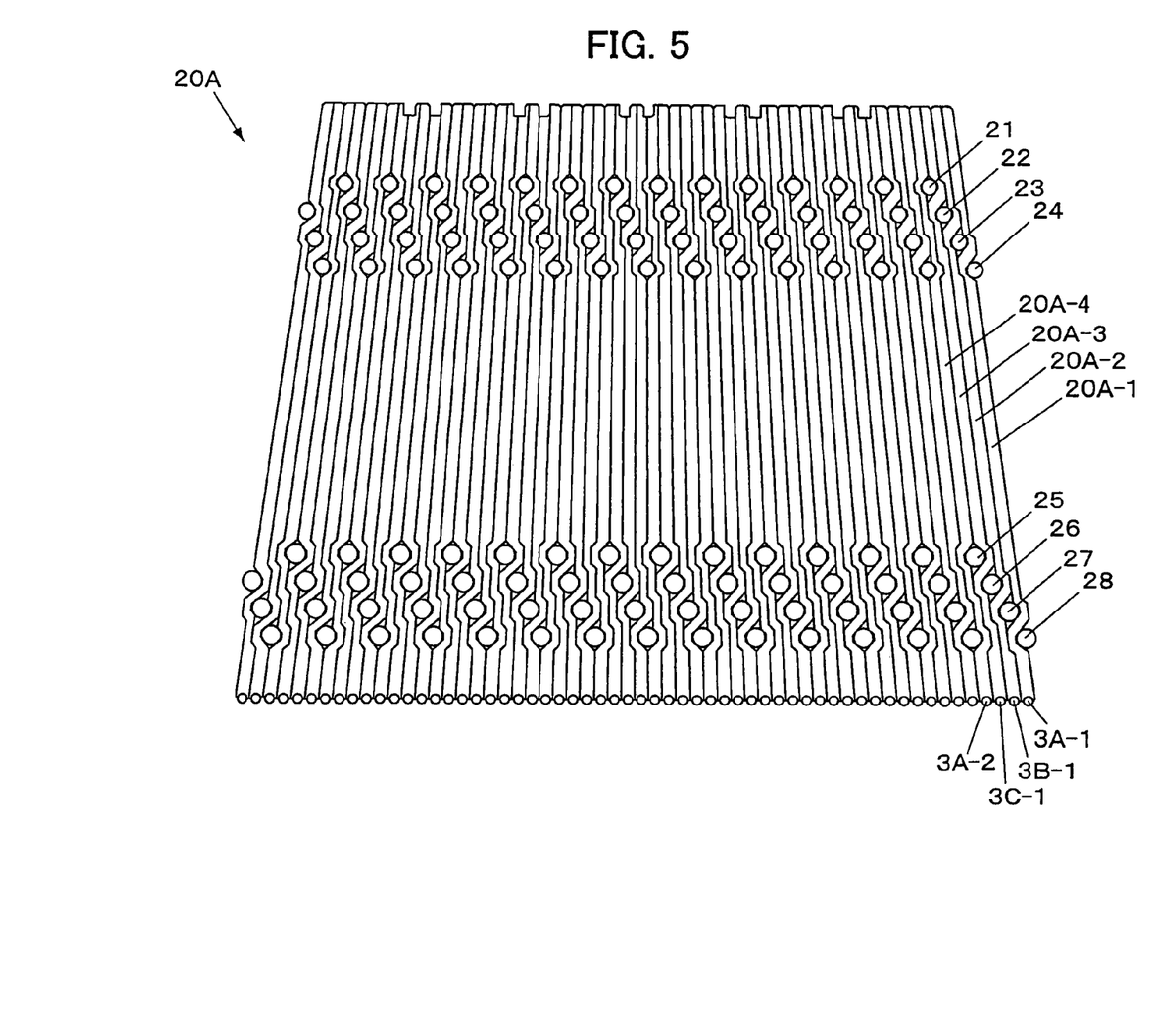
FIG. 5 is a view showing an aperture leaf 20A according to a third embodiment of the present invention.

FIG. 5 is a view showing an aperture leaf 20A according to a third embodiment of the present invention (corresponding to the cross-sectional view along the line D-D in FIG. 1 showing the first embodiment).

The aperture leaf 20A includes aperture leaves which are arranged in the thickness direction so that the aperture leaves can freely move through rolling elements. The aperture leaves 20A-1 to 20A-4 are described below. As shown in FIG. 5, when the shape of the aperture leaves 20A-1 to 20A-4 is considered as one pattern, the aperture leaf 20A is formed by repeatedly arranging the aperture leaves 20A-1 to 20A-4 in the thickness direction (described later).

The aperture leaves 20A-1 to 20A-4 are arranged in the thickness direction so that the aperture leaves 20A-1 to 20A-4 can freely move through rolling elements 21 to 28. As shown in FIG. 5, the side surfaces of the aperture leaves 20A-1 to 20A-4 protrude in the thickness direction to form holding portions which hold the rolling elements 21 to 28. Therefore, even when the aperture leaves 20A-1 to 20A-4 are driven and an opening occurs between the aperture leaves, strong radiation can be prevented from passing through the space between the aperture leaves 20A-1 to 20A-4. Specifically, the holding portions hold the rolling elements 21 to 28 and function as shielding portions which shield radiation.

The strength of the aperture leaves 20A-1 to 20A-4 can be maintained at a value equal to or higher than a specific value by adjusting the thicknesses of the aperture leaves 20A-1 to 20A-4 forming the holding portions and the size of the rolling elements 21 to 28 to values equal to or higher than specific values.

The rolling elements 21 to 28 may have an appropriate shape (e.g., ball shape, cylindrical, or conical trapezoidal) insofar as the rolling elements 21 to 28 function as bearings when the aperture leaves 20A-1 to 20A-4 are respectively driven using the linear members 3A-1, 3B-1, 3C-1, and 3A-2.

The rolling elements 21 to 24 are disposed at a position closer to the radiation source 1 than the rolling elements 25 to 28, and have a diameter smaller than that of the rolling elements 25 to 28. The aperture leaves 20A-1 to 20A-4 are smoothly driven using the linear members 3A-1, 3B-1, 3C-1, and 3A-2.

The arrangement of the rolling elements 23 and 24 and the rolling elements 27 and 28 adjacent on either side of one aperture leaf (e.g. aperture leaf 20A-1) is described below.

The rolling element 23 is disposed at a position close to the radiation source 1, and the rolling element 24 is disposed at a position away from the radiation source 1. Likewise, the rolling element 27 is disposed at a position close to the radiation source 1, and the rolling element 28 is disposed at a position away from the radiation source 1.

Therefore, the thickness of the entire aperture leaf 20A does not change depending on the size of the rolling elements 21 to 28. For example, a rolling element having a diameter almost equal to the thickness of the aperture leaf 20A-1 may be held using the holding portion. Since the opening between the aperture leaves 20A-1 and 20A-2 is uniformly maintained by the rolling elements 23 and 27, a situation can be prevented in which the frictional resistance increases due to contact between the aperture leaves 20A-1 and 20A-2, whereby a large amount of load is applied to the linear member 3, the driver section 10, and the like.

The holding portions are formed of a straight line and/or a curve formed by bending or cutting the aperture leaves 20A-1 to 20A-4. As a result, the holding portions can be formed even if the thicknesses of the aperture leaves 20A-1 to 20A-4 are reduced.

As shown in FIG. 5, the holding portions are disposed at different positions with respect to the irradiation direction (see FIG. 1). The holding portions are repeatedly disposed at an identical position in units of a specific number (four in this embodiment) of aperture leaves 20A-1 to 20A-4. Therefore, the aperture leaf 20A allows the holding portions to be formed by repeatedly arranging the aperture leaves of the same shape in units of a specific number. As a result, the number of types of bending or cutting can be set at a specific value when forming the aperture leaf 20A, whereby the aperture leaf 20A can be quickly formed at reduced cost.

Fourth Embodiment

Figure 6A:
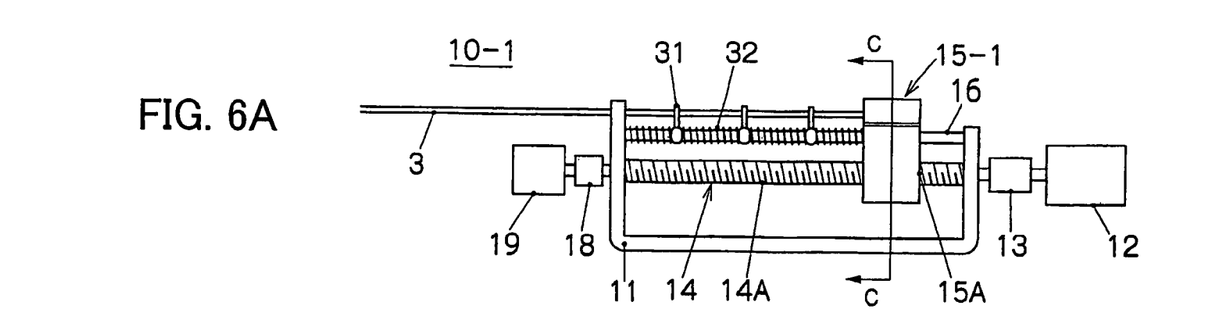
FIG. 6A to 6C are view showing a driver section 10-1 according to a fourth embodiment of the present invention.
Figure 6B:
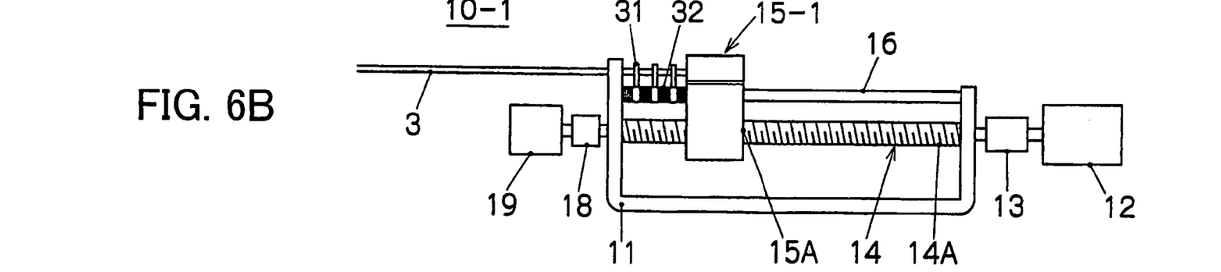
Figure 6C:
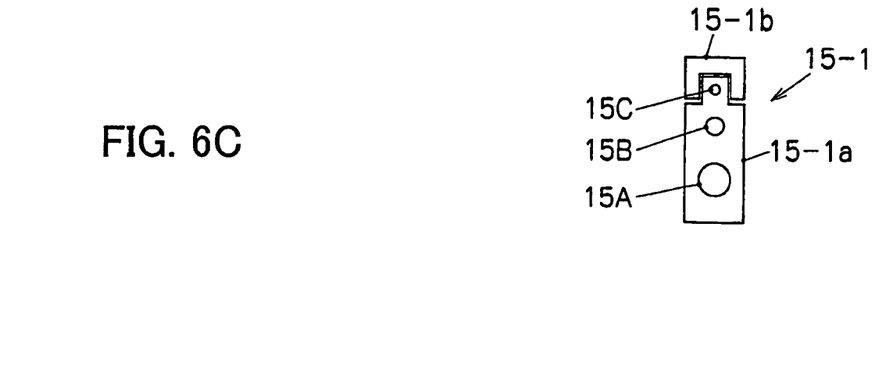

FIGS. 6A to 6C are view showing a driver section 10-1 according to a fourth embodiment of the present invention. FIG. 6C is a view as seen from the direction of C-C in FIG. 6A. Note that description of the functions and the like of the same members as those of the above-described driver section 10 is appropriately omitted.

The driver section 10-1 differs from the driver section 10 in that the driver section 10-1 includes a slider 15-1, a guide 31, an elastic member 32 (coil spring in FIG. 6A or 6B), and the like which are provided in the base 11, for example.

The slider 15-1 can move in the axial direction of the drive shaft 14 accompanying the rotation of the drive shaft 14, and includes a pedestal portion 15-1a and an engagement portion 15-1b connected with the pedestal section 15-1a. The pedestal section 15-1a includes a female thread portion 15A which engages the male thread portion 14A of the drive shaft 14, a support hole 15B through which the support shaft 16 passes, and a joint portion 15C connected with the linear member 3.

The guide 31 is supported on the support shaft 16, can move in the axial direction of the support shaft 16, and maintains the shape of the linear member 3. The elastic member 32 supported on the support shaft 16 is disposed between the guides 31.

In FIG. 6A, illustrates a state in which the linear member 3 is pulled into the base 11 by the slider 15-1 (i.e. a state in which the aperture leaf 20A is pulled out in the direction in which the irradiation field A is enlarged). In this case, since the linear member 3 can freely move in the base 11 in the driver section 10 (see FIG. 1), the linear member 3 may buckle when the slider 15 pushes the linear member 3 out of the base 11.

In order to prevent the linear member 3 from buckling in the base 11, the driver section 10-1 according to this embodiment includes the guides 31 supported on the support shaft 16 and the elastic member 32 disposed between the guides 31. The elastic member 32 can maintain the interval between the guides 31 approximately identical, even if the guides 31 have moved in the axial direction of the support shaft 16.

The interval between the guides 31 is determined by the length of the elastic member 32. As the elastic member 32, an appropriate elastic member other than the coil spring may be used insofar as the interval between the guides 31 can be maintained approximately identical.

In FIG. 6B, illustrates a state in which the linear member 3 is pushed out from the base 11 by the slider 15-1 (i.e. a state in which the aperture leaf 20A is pushed in the direction in which the irradiation field A is reduced). In this case, since only a small portion of the linear member 3 freely moves in the base 11 and the elastic member 32 provided between the guides 31 shrinks, the interval between the guides 31 is reduced, whereby the linear member 3 can be reliably prevented from buckling.

Fifth Embodiment

Figure 7:
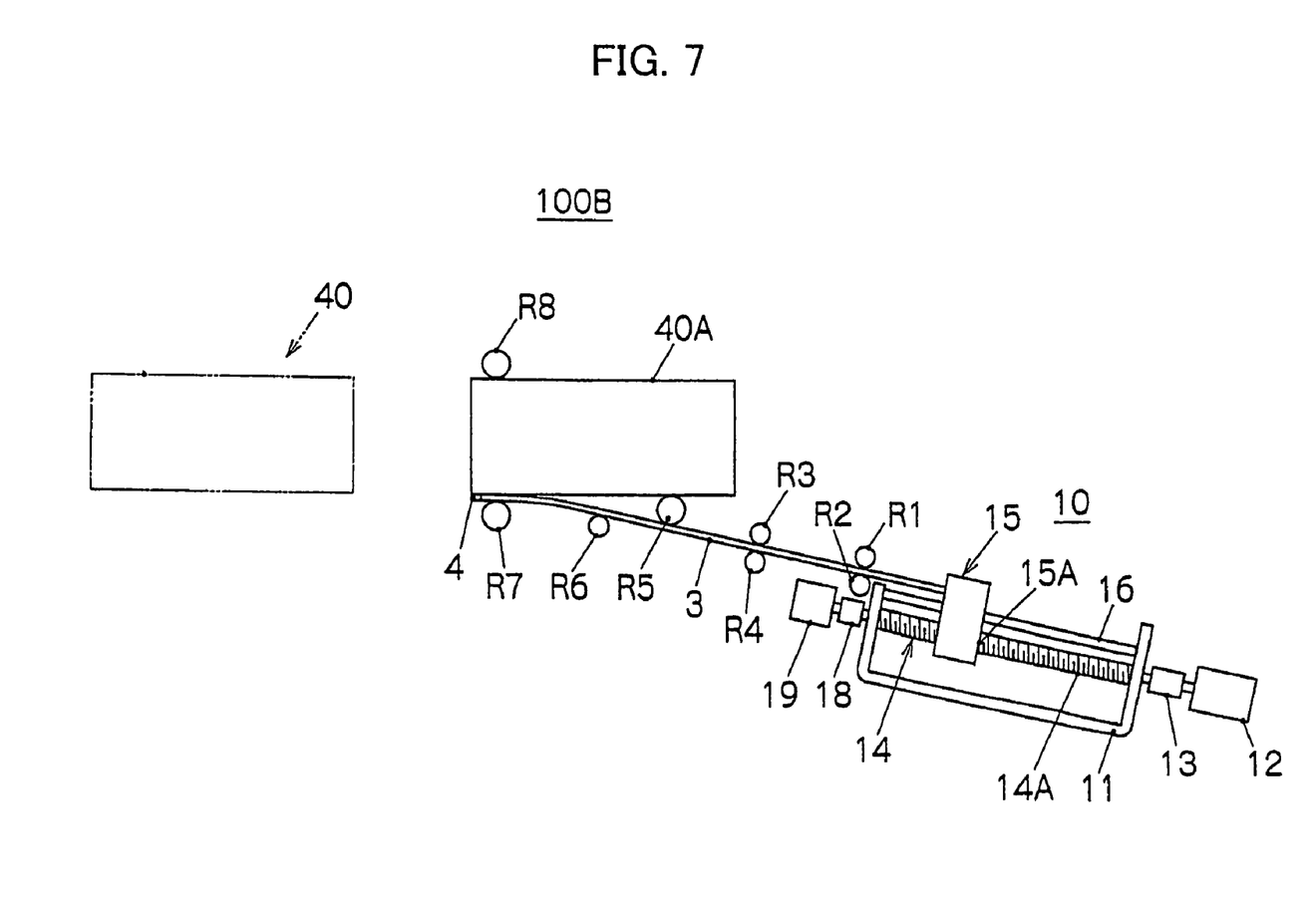
FIG. 7 is a view showing an irradiation field limiting device 100B according to a fifth embodiment of the present invention.

FIG. 7 is a view showing an irradiation field limiting device 100B according to a fifth embodiment of the present invention.

The irradiation field limiting device 100B differs from the irradiation field limiting device 100 according to the first embodiment in that one end of the linear member 3 is secured to an approximately rectangular aperture leaf 40 (aperture leaf 40A in FIG. 7) through the connection section 4 tangentially to the shape on the outer circumference of the aperture leaf 40.

The other end of the linear member 3 is connected with the slider 15 provided in the driver section 10. The approximately rectangular aperture leaf 40A is driven a specific amount along a path guided by the rollers R5, R7, and R8 along with the movement of the slider 15.

According to the irradiation field limiting device 100B, even if the aperture leaf 40A is approximately rectangular, the aperture leaf 40A can be accurately driven along the path by securing the flexible linear member 3 to the aperture leaf 40A.

(Modification)

The present invention is not limited to the above-described embodiments, and various modifications and variations may be made. Such modifications and variations are also within the scope of the equivalence of the present invention.

(1) In the driver sections 10 and 10-1, the slider 15 is driven in the axial direction of the drive shaft 14 by causing the male thread portion 14A formed in the drive shaft 14 connected with the driving source 12 to engage the female thread portion 15A of the slider 15. Note that the present invention is not limited thereto. An appropriate drive method (e.g. method of driving the slider 15 using a hydraulic mechanism or a pneumatic mechanism) may be used insofar as the driving force of the driving source 12 can be transmitted to the slider 15.

(2) In the driver sections 10 and 10-1, one drive shaft 14 is driven using one driving source 12. Note that the present invention is not limited thereto. A plurality of drive shafts 14 may be driven using one driving source.

In more detail, a pulley (or a gear) or the like corresponding to the position of each drive shaft 14 is provided to the drive shaft connected with one driving source, and a belt (or a gear which engages the gear provided to the drive shaft) or the like connected with the pulley is provided on one end of each drive shaft 14. This allows the driving force of one driving source to be transmitted to each drive shaft 14 through the pulley, the gear, and the like.

When applying radiation to the lesion of a radiotherapy target subject, it is necessary to accurately form an irradiation field corresponding to the shape of the lesion in a short time. Accordingly, the required driving amount differs for each of the arranged aperture leaves 20 and 40.

Therefore, a control section is provided which controls the clutch mechanism of the connection portion 13 of each of the aperture leaves 20 and 40, and the control section calculates the driving amount of each drive shaft 14 required for each of the aperture leaves 20 and 40 and the transmission time of the driving force of one driving source using the clutch mechanism corresponding to the driving amount based on the absolute position information of the aperture leaves 20 and 40 and/or the slider 15 and the relative position information of the slider 15. According to this control section, the driving force of one driving source can be transmitted for a period of time necessary for each drive shaft 14 corresponding to the driving amount of each drive shaft 14 corresponding to the arranged aperture leaves 20 and 40, whereby the drive shafts 14 can be accurately controlled using one driving source, and the irradiation field can be accurately formed in a short time.

Moreover, since a different driving source 12 need not be disposed for each drive shaft 14, the installation space can be reduced, whereby a driving source with a certain size (e.g. driving source exhibiting high abrasion resistance and a large torque, such as a servomotor, pulse motor, or brushless DC motor) can be applied.

(3) In the aperture leaf 20A, the rolling elements 21 to 24 are disposed at positions on the aperture leaf 20A closer to the radiation source 1, and the rolling elements 25 to 28 are disposed at positions away from the radiation source 1. Note that the number and the positions of the rolling elements are not limited thereto insofar as the aperture leaf 20A can be arranged to freely move. An appropriate number of rolling elements may be provided. Another rolling element may be disposed at a position approximately between the rolling elements 21 to 24 and the rolling elements 25 to 28.

(4) In the irradiation field limiting device 100, the driver section 10 is disposed so that one end of the linear member 3 is secured to the outer circumference of the aperture leaf 20A. Note that the driver section 10 may be disposed so that one end of the linear member 3 is secured to the inner circumference of the aperture leaf 20A insofar as the aperture leaf 20A can be driven.

(5) The aperture leaves 20 and 40 respectively have a fan shape and an approximately rectangular shape. Note that the aperture leaves 20 and 40 may have an appropriate shape insofar as the aperture leaf can be connected with the linear member 3 and radiation from the radiation source 1 can be shielded along with the movement of the linear member 3.

(6) In the first embodiment, the potentiometer 5 directly measures the absolute position of the outer circumference of the aperture leaf 20A. Note that the invention is not limited thereto. For example, the potentiometer 17 (indicated by the dash-dot-dot line) may be provided in the driver section 10, as shown in FIGS. 1 and 2. The displacement of the slider 15 may be measured, and the position of the aperture leaf 20A may be determined from the amount of movement of the linear member 3.

If the driver sections are provided in units of the axial directions of the linear members 3 as in the second embodiment, the irradiation field limiting device can have a thickness necessary for the potentiometer (e.g. when the thickness of the aperture leaf 20A is 3 mm and the number of axial directions of the linear members 3 is three, the thickness of the potentiometer 17 may be 9 mm or less). Even if the thickness of the aperture leaf 20A is reduced, the potentiometer 17 can have a necessary thickness (e.g., when the thickness of the aperture leaf 20A is set at 1 mm, the thickness of the potentiometer 17 may be set at 3 mm or less).

(7) In the first embodiment, the irradiation field limiting device 100 measures the amount of movement of the slider 15 using the encoder 19 (relative position sensor) to accurately control and drive the aperture leaf 20A. Note that the invention is not limited thereto. For example, the amount of movement of the aperture leaf 20A from the reference position (specific position) may be measured using a linear encoder. This also allows the irradiation field limiting device 100 to accurately control and drive the aperture leaf 20A.

(8) In the second embodiment, the driver section includes the slider 15. Note that the invention is not limited thereto. Since it suffices that a thickness required for the driver section be provided and the linear member 3 be driven in the axial direction, the irradiation field limiting device may include a mechanism such as a rack and a pinion gear. In this case, the driver section can accurately drive the aperture leaf, even if a gap is formed between the rack and the pinion gear, by using the potentiometer or the like. Moreover, the driver section can prevent breakage of the driving source or the like by providing a driving force limiting section (e.g. ball torque limiter) in the drive shaft of the pinion gear.

(9) In each embodiment, the driver section drives the aperture leaf by causing the drive shaft 14 to engage the slider 15. Note that the invention is not limited thereto. For example, when the aperture leaf 20 has a large thickness and weight, the drive shaft 14 and the slider 15 may be connected using a ball screw. This allows the driver section to smoothly rotate the drive shaft 14, whereby the aperture leaf 20 can be stably driven, even if the aperture leaf 20 has a large weight.

(10) In the first embodiment, only the encoder 19 for measuring the number of rotations of the drive shaft 14 is provided. Note that the invention is not limited thereto. For example, a driving source measurement encoder may be provided to measure the number of rotations of the driving source 12 in addition to the encoder 19. Since the number of rotations of the drive shaft 14 differs from the number of rotations of the driving source in a state in which the torque limiter mechanism operates, the control section may be allowed to monitor the output from the driving source measurement encoder with the encoder 19, and the driving source may be stopped when a difference has been monitored between the number of rotations of the drive shaft 14 and the number of rotations of the driving source. As a result, when using a mechanical torque limiter (torque limiter section), excess wear of the contact surface can be prevented. The irradiation field limiting device can prevent extended operation of a motor (driving source) at a high load, whereby breakage of the motor can be prevented.

What is claimed is:

1. An irradiation field limiting device which shields radiation from a radiation source by driving a plurality of aperture leaves a specific amount to limit an irradiation field to a desired range, the irradiation field limiting device comprising:

a plurality of aperture leaves each having a circumferential shape;
a driver section; and
a flexible linear member, one end thereof being secured to at least one aperture leaf and the other end being connected to the driver section, the driver section being configured to drive the flexible linear member in an axial direction of the flexible linear member to cause movement of the at least one aperture leaf,
wherein the aperture leaves are arranged in a thickness direction thereof adjacent to each other, the one end of the flexible linear member is secured to an inner or outer circumferential surface of the at least one aperture leaf, and the driver section drives the flexible linear member while increasing or decreasing a contact portion between the flexible linear member and the inner or outer circumferential surface of the at least one aperture leaf by warping the flexible linear member, and
wherein the driver section includes:
a base;
a drive shaft connected with a driving source through a connection portion and inserted into the base; and
a slider which moves along an axial direction of the drive shaft accompanying rotation of the drive shaft and is connected with the linear member.

2. The irradiation field limiting device according to claim 1,
wherein the connection portion includes a torque limiter section which limits transmission of torque equal to or greater than a specific torque.

3. The irradiation field limiting device according to claim 2,
wherein the connection portion includes a clutch mechanism which transmits a driving force to the drive shaft or disconnects the driving force from the drive shaft; and
wherein the irradiation field limiting device includes a control section which prevents the driving force from being transmitted to the drive shaft using the clutch mechanism when the torque limiter section has operated for a specific period of time.

4. The irradiation field limiting device according to claim 1,
wherein the connection portion includes a clutch mechanism which transmits a driving force to the drive shaft or disconnects the driving force from the drive shaft; and
wherein the irradiation field limiting device includes:
a position detection section which detects a position of the aperture leaves; and
a control section which prevents the driving force from being transmitted to the drive shaft using the clutch mechanism to stop movement of the aperture leaves when the position detection section has detected that the aperture leaves have moved to a target position.

5. The irradiation field limiting device according to claim 1, comprising:
a driving force transmission section which transmits a driving force of the driving source to a plurality of the drive shafts;
a plurality of clutch mechanisms which transmit the driving force to the drive shafts or disconnect the driving force from the drive shafts; and
a control section configured to drive each of the aperture leaves by transmitting the driving force of the driving source in units of the drive shafts by controlling each of the clutch mechanisms.

6. The irradiation field limiting device according to claim 1,
wherein the slider has a female thread portion; and
wherein the drive shaft has a male thread portion which engages the female thread portion and moves the slider in the axial direction of the drive shaft by being rotated.

7. The irradiation field limiting device according to claim 1, wherein the aperture leaf is fan-shaped or approximately rectangular.

8. The irradiation field limiting device according to claim 1,
wherein the linear member comprises a continuous metal wire, a wire rope formed by twisting metal wires, or a hollow pipe.

9. The irradiation field limiting device according to claim 1, comprising:
a support shaft provided in the base and disposed approximately in parallel with the drive shaft at a specific interval from the drive shaft;
at least one guide which is supported on the support shaft so that the guide moves in an axial direction of the support shaft and maintains a shape of the linear member; and
an elastic member which is disposed between the guides and maintains an approximately identical interval between the guides.

10. The irradiation field limiting device according to claim 1, comprising:
an absolute position sensor which measures an absolute position of at least one of the at least one aperture leaf and the slider; and
a high-resolution relative position sensor which measures an amount of movement from a specific position of at least one of the at least one aperture leaf and the slider measured using the absolute position sensor.

11. The irradiation field limiting device according to claim 1,
wherein the aperture leaves are arranged in the thickness direction so that the aperture leaves freely move through rolling elements; and
wherein a side surface of each aperture leaf protrudes in the thickness direction to form a holding portion which holds each rolling element.

12. The irradiation field limiting device according to claim 11,
wherein the holding portion forms at least one of a straight line and a curve to hold each rolling element.

13. The irradiation field limiting device according to claim 11,
wherein one of adjacent rolling elements provided on either side of each aperture leaf is disposed at a position close to the radiation source, and the other is disposed at a position away from the radiation source.

14. The irradiation field limiting device according to claim 11,
wherein holding portions are disposed at different positions with respect to the irradiation direction, and are repeatedly disposed at an identical position in units of a specific number of the aperture leaves.

15. The irradiation field limiting device according to claim 11,
wherein the holding portion is a shielding portion which prevents radiation from passing through a space between the aperture leaves adjacent to each other.

16. The irradiation field limiting device according to claim 1, comprising:
a shielding portion which shields radiation in an opening between the aperture leaves adjacent to each other.

17. The irradiation field limiting device according to claim 1,
wherein linear members respectively secured to the aperture leaves adjacent in the thickness direction differ in axial direction.

18. The irradiation field limiting device according to claim 17,
wherein the driver section drives the at least one aperture leaf of which the axial direction of the linear member is set to be identical in units of a specific number of the linear members.

19. The irradiation field limiting device according to claim 1,
wherein linear members respectively secured to the aperture leaves adjacent in the thickness direction differ in axial direction and are identical in axial direction in units of a specific number of the linear members; and
wherein the irradiation field limiting device includes a plurality of driver units each of which includes a plurality of driver sections which respectively drive the linear members of which the axial directions are set to be identical in units of a specific number of the linear members.

20. The irradiation field limiting device according to claim 1, comprising:
a linear member holding portion which holds the linear member between the at least one aperture leaf and the driver section so that the linear member moves in the axial direction to prevent the linear member from buckling.

21. The irradiation field limiting device according to claim 1,
wherein the linear member drives the at least one aperture leaf while contacting the thick portion, is preliminarily bent in a direction away from a contact portion between the linear member and the thick portion, and presses a portion in contact with the thick portion so that the linear member is prevented from buckling.

* * * * *